US012171261B2

(12) United States Patent
Aller et al.

(10) Patent No.: US 12,171,261 B2
(45) Date of Patent: Dec. 24, 2024

(54) VAPORIZATION SYSTEM

(71) Applicant: RAI Strategic Holdings, Inc., Winston-Salem, NC (US)

(72) Inventors: Jared Aller, Winston-Salem, NC (US); Charles Jacob Novak, III, Winston-Salem, NC (US); Michael Ryan Galloway, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 839 days.

(21) Appl. No.: 16/189,459

(22) Filed: Nov. 13, 2018

(65) Prior Publication Data

US 2020/0113240 A1      Apr. 16, 2020

Related U.S. Application Data

(60) Provisional application No. 62/744,978, filed on Oct. 12, 2018.

(51) Int. Cl.
*A24F 40/42* (2020.01)
*A24B 15/167* (2020.01)
(Continued)

(52) U.S. Cl.
CPC ............ *A24F 40/42* (2020.01); *A24B 15/167* (2016.11); *A24D 1/002* (2013.01); *A24D 1/14* (2013.01); *A24F 7/00* (2013.01); *A24F 7/02* (2013.01); *A24F 40/46* (2020.01); *A61M 11/042* (2014.02); *H01R 13/17* (2013.01); *H01R 13/6205* (2013.01); *H05B 3/20* (2013.01); *A24F 40/40* (2020.01); *A61M 11/041* (2013.01); *A61M 2205/0288* (2013.01);
(Continued)

(58) Field of Classification Search
CPC ................................ A24D 3/17; A24F 47/002
See application file for complete search history.

(56) References Cited

U.S. PATENT DOCUMENTS 2,057,353 A    10/1936    Whittemore, Jr.
2,104,266 A     1/1938    McCormick
(Continued)

FOREIGN PATENT DOCUMENTS

CN      1541577      11/2004
CN      2719043       8/2005
(Continued)

OTHER PUBLICATIONS

CN Office Action dated Dec. 29, 2023 from related CN Application No. 201980082961.2, filed Jun. 15, 2021; 13 pages.

*Primary Examiner* — Michael H. Wilson
*Assistant Examiner* — Stephanie Lynn Moore
(74) *Attorney, Agent, or Firm* — WOMBLE BOND DICKINSON (US) LLP

(57) ABSTRACT

The present disclosure relates to vaporization systems and interchangeable elements forming such systems. In particular, a plurality of control devices may be interchangeably combined with one or more cartridges to provide an overall vaporization system that provide customizable vaporization characteristics for a consumer. The vaporization system further can include at least one external connection device for charging and/or data communication.

23 Claims, 5 Drawing Sheets

(51) Int. Cl.

| | | |
|---|---|---|
| *A24D 1/00* | (2020.01) | |
| *A24D 1/14* | (2006.01) | |
| *A24F 7/00* | (2006.01) | |
| *A24F 7/02* | (2006.01) | |
| *A24F 40/40* | (2020.01) | |
| *A24F 40/46* | (2020.01) | |
| *A61M 11/04* | (2006.01) | |
| *H01R 13/17* | (2006.01) | |
| *H01R 13/62* | (2006.01) | |
| *H05B 3/20* | (2006.01) | |

(52) U.S. Cl.
CPC . *A61M 2205/3368* (2013.01); *A61M 2205/50* (2013.01); *A61M 2205/584* (2013.01); *A61M 2205/587* (2013.01); *A61M 2205/8206* (2013.01); *H05B 2203/021* (2013.01)

(56) References Cited

U.S. PATENT DOCUMENTS

| | | |
|---|---|---|
| 3,200,819 A | 8/1965 | Gilbert |
| 4,922,901 A | 5/1990 | Brooks et al. |
| 5,060,671 A | 10/1991 | Counts et al. |
| 5,093,894 A | 3/1992 | Deevi et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Terry et al. |
| 8,365,742 B2 | 2/2013 | Hon |
| 8,499,766 B1 | 8/2013 | Newton |
| 8,528,569 B1 | 9/2013 | Newton |
| 8,833,364 B2 | 9/2014 | Buchberger |
| 9,220,304 B2 | 12/2015 | Greim |
| 9,462,831 B2 | 10/2016 | Liu |
| 9,737,093 B2 | 8/2017 | Hon |
| 9,877,508 B2 | 1/2018 | Kane |
| 10,015,990 B2 | 7/2018 | Mironov |
| 10,028,537 B1 | 7/2018 | Hawes et al. |
| 10,039,321 B2 | 8/2018 | Verleur et al. |
| 10,058,123 B2 | 8/2018 | Taluskie et al. |
| 10,058,125 B2 | 8/2018 | Worm et al. |
| 10,076,139 B2 | 9/2018 | Monsees et al. |
| 10,080,851 B2 | 9/2018 | Davidson et al. |
| 10,085,481 B2 | 10/2018 | Verleur et al. |
| 10,092,037 B2 | 10/2018 | Tucker et al. |
| 10,104,913 B2 | 10/2018 | Lau et al. |
| 10,117,463 B2 | 11/2018 | Thomas |
| 10,117,467 B2 | 11/2018 | Hawes et al. |
| 10,206,429 B2 | 2/2019 | Davis et al. |
| 10,226,076 B2 | 3/2019 | Althorpe et al. |
| 10,279,934 B2 | 5/2019 | Christensen et al. |
| 10,869,505 B2 | 12/2020 | Borkovec et al. |
| 11,089,660 B2 | 8/2021 | Wensley et al. |
| 2005/0016550 A1 | 1/2005 | Katase |
| 2006/0196518 A1 | 9/2006 | Hon |
| 2008/0092912 A1 | 4/2008 | Robinson et al. |
| 2009/0095311 A1 | 4/2009 | Hon |
| 2009/0126745 A1 | 5/2009 | Hon |
| 2009/0151717 A1 | 6/2009 | Bowen et al. |
| 2009/0188490 A1 | 7/2009 | Hon |
| 2009/0272379 A1 | 11/2009 | Thorens et al. |
| 2009/0320863 A1 | 12/2009 | Fernando et al. |
| 2011/0094523 A1* | 4/2011 | Thorens ............... H05B 1/0202 131/194 |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2013/0037041 A1 | 2/2013 | Worm et al. |
| 2013/0042865 A1* | 2/2013 | Monsees ............ G05D 23/1917 128/203.27 |
| 2013/0087160 A1* | 4/2013 | Gherghe ................... A24F 1/00 131/329 |
| 2013/0168880 A1* | 7/2013 | Duke ................... A24F 47/008 261/78.2 |
| 2013/0306084 A1 | 11/2013 | Flick |
| 2013/0319435 A1 | 12/2013 | Flick |
| 2014/0000638 A1 | 1/2014 | Sebastian et al. |
| 2014/0041655 A1 | 2/2014 | Barron et al. |
| 2014/0096781 A1 | 4/2014 | Sears et al. |
| 2014/0096782 A1 | 4/2014 | Ampolini et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0366898 A1 | 12/2014 | Monsees et al. |
| 2015/0020832 A1 | 1/2015 | Greim et al. |
| 2015/0150308 A1 | 6/2015 | Monsees et al. |
| 2015/0164142 A1 | 6/2015 | Li et al. |
| 2015/0208729 A1 | 7/2015 | Monsees et al. |
| 2015/0313287 A1 | 11/2015 | Verleur et al. |
| 2016/0345629 A1* | 12/2016 | Mironov ............... A61M 11/042 |
| 2017/0027226 A1 | 2/2017 | Mironov et al. |
| 2017/0071256 A1 | 3/2017 | Verleur et al. |
| 2017/0095005 A1 | 4/2017 | Monsees et al. |
| 2017/0135404 A1 | 5/2017 | Reevell |
| 2017/0135405 A1 | 5/2017 | Reevell |
| 2017/0143042 A1 | 5/2017 | Batista et al. |
| 2017/0215485 A1 | 8/2017 | Zitzke |
| 2017/0231281 A1 | 8/2017 | Hatton et al. |
| 2017/0231282 A1 | 8/2017 | Hatton et al. |
| 2017/0251722 A1 | 9/2017 | Kobal et al. |
| 2017/0325289 A1 | 11/2017 | Liu |
| 2017/0340011 A1* | 11/2017 | Batista ................ A24F 47/008 |
| 2017/0340012 A1 | 11/2017 | Mironov et al. |
| 2017/0347711 A1 | 12/2017 | Litten et al. |
| 2017/0347712 A1 | 12/2017 | Singh |
| 2018/0000157 A1 | 1/2018 | Batista et al. |
| 2018/0000160 A1 | 1/2018 | Taschner et al. |
| 2018/0014575 A1 | 1/2018 | Fursa |
| 2018/0020731 A1 | 1/2018 | Rasmussen et al. |
| 2018/0020736 A1 | 1/2018 | Silvestrini |
| 2018/0035717 A1 | 2/2018 | Batista |
| 2018/0042306 A1 | 2/2018 | Atkins et al. |
| 2018/0043114 A1 | 2/2018 | Bowen et al. |
| 2018/0070645 A1* | 3/2018 | Monsees ............... A61M 11/042 |
| 2018/0077967 A1 | 3/2018 | Hatton et al. |
| 2018/0084828 A1 | 3/2018 | Phillips et al. |
| 2018/0084831 A1 | 3/2018 | Mironov |
| 2018/0103685 A1* | 4/2018 | Yener ................... A24F 47/008 |
| 2018/0132525 A1 | 5/2018 | Patil et al. |
| 2018/0140019 A1 | 5/2018 | Guo et al. |
| 2018/0153220 A1 | 6/2018 | Verleur et al. |
| 2018/0177230 A1 | 6/2018 | Hawes et al. |
| 2018/0213850 A1 | 8/2018 | Brinkley et al. |
| 2018/0242643 A1 | 8/2018 | Silvestrini et al. |
| 2018/0280637 A1 | 10/2018 | Mayle et al. |
| 2018/0295888 A1 | 10/2018 | Newcomb et al. |
| 2018/0296777 A1 | 10/2018 | Terry et al. |

FOREIGN PATENT DOCUMENTS

| | | |
|---|---|---|
| CN | 201379072 | 1/2010 |
| CN | 104621716 A | 5/2015 |
| CN | 107072314 A | 8/2017 |
| CN | 108289505 A | 7/2018 |
| EP | 1 618 803 | 1/2006 |
| JP | 2017533726 A | 11/2017 |
| KR | 20160082576 A | 7/2016 |
| WO | WO 2004/080216 | 9/2004 |
| WO | WO 2005/099494 | 10/2005 |
| WO | WO 2007/131449 | 11/2007 |
| WO | WO 2016/026811 | 2/2016 |
| WO | WO 2017/051006 | 9/2016 |
| WO | WO 2017/207442 | 5/2017 |
| WO | WO 2018/167166 | 9/2018 |
| WO | WO 2018/202732 | 11/2018 |

* cited by examiner

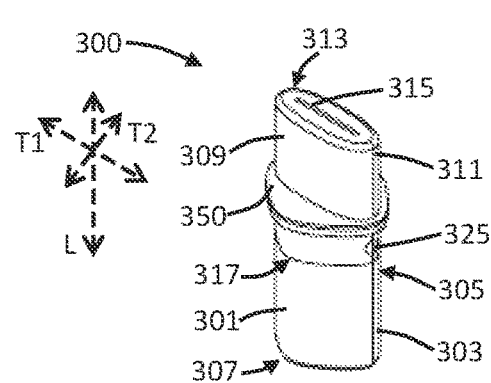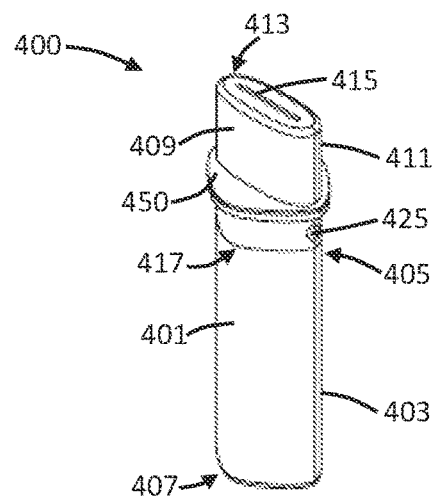
FIG. 5　　　　　　FIG. 6
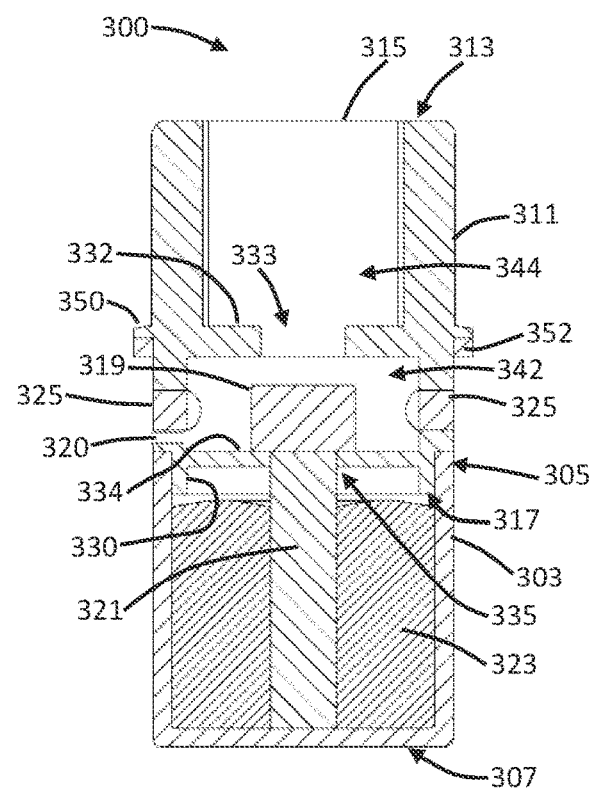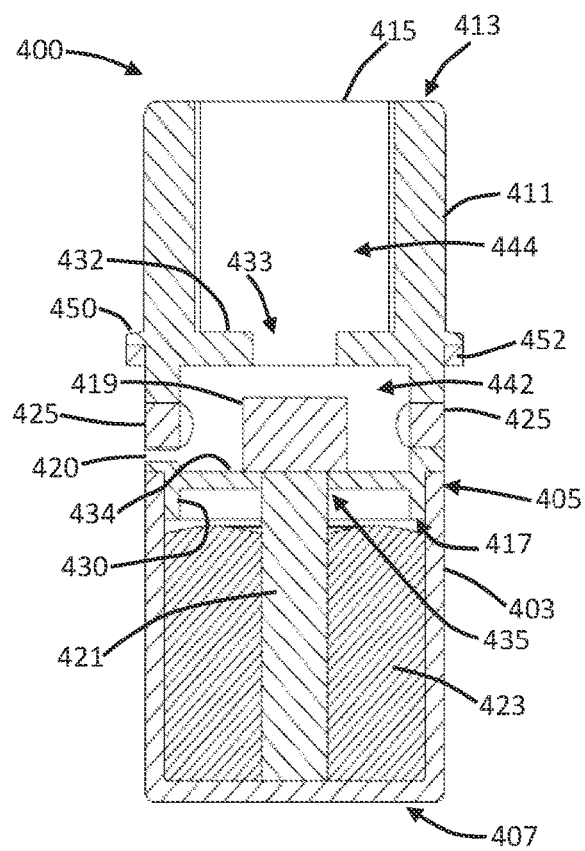
FIG. 7　　　　　　FIG. 8

VAPORIZATION SYSTEM

CROSS-REFERENCE TO RELATED APPLICATIONS

The present application claims priority to U.S. Provisional Patent Application No. 62/744,978, filed Oct. 12, 2018, the disclosure of which is incorporated herein by reference in its entirety.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference.

It would be desirable to provide a vaporization system providing consumers with improved customization ability. It would further be desirable to provide a vaporization system including a plurality of elements that are interchangeable so that the consumer has a single system with interchangeable parts that provides different vaporization properties as may be desired by the consumer.

SUMMARY OF THE DISCLOSURE

The present disclosure relates to aerosol delivery devices, methods of forming such devices, and elements of such devices. The disclosure particularly can relate to an aerosol delivery system formed of a one or a plurality of cartridges that are interchangeably connectable to one or a plurality of devices, which in turn are connectable to an external connector (e.g., for charging and/or for data or information transfer).

In one or more embodiments, the present disclosure thus can provide a vaporization system. In an example embodiment, such vaporization can comprise: a control device having: a device outer housing defining a device outer wall, a device distal end, and a device proximal end that includes an opening formed therein; a device chamber defined by a device inner frame having at least a chamber sidewall and a chamber bottom wall, the opening in the device proximal end providing access into the device chamber; a device battery positioned within the device outer housing; a device printed circuit board assembly (PCBA) positioned within the device outer housing; device electrical connectors positioned in the first device chamber so as to not be positioned on the chamber bottom wall; and a device external connection element; a cartridge comprising: a tank defined by an outer tank wall that includes a proximal end and a closed, distal end, the tank being configured to contain a liquid composition; a mouthpiece defined by an outer mouthpiece wall that includes a proximal end with an exit portal and a distal end that is engaging the proximal end of the tank; a heater; a liquid transport element; and electrical contacts that are not positioned on the closed, distal end of the tank; wherein the cartridge is configured to engage the control device such that at least a portion of the tank of the cartridge is received within the device chamber to form the vaporization system in a functioning combination with the electrical contacts of the cartridge electrically engaging the device electrical connectors. In further embodiments, such vaporization system can be defined in relation to one or more of the following statements, which can be combined in any number and order.

The vaporization system can comprise a first control device and a second control device, wherein the first control device and the second control device are interchangeably connectable with the cartridge such that at least a portion of the tank of the cartridge is separately receivable within each of a first device chamber present in the first device and a second device chamber present in the second device to form the vaporization system in a functioning combination, and wherein the first control device differs from the second control device.

The first control device can differ from the second control device in one or more of the following aspects: the first device comprises a first device outer housing, and the second device comprises a second device outer housing, and the first device outer housing and the second device outer housing are each formed of a different material; the first device comprises a first device battery, and the second device comprises a second device battery, and the first device battery is different from the second device battery; the first device comprises a first device PCBA, and the second device comprises a second device PCBA, and the first device PCBA is different from the second device PCBA; and the first device comprises a first device external connection element, and the second device comprises a second device external connection element, and the first device external connection element is different from the second device external connection element.

The first device battery can differ from the second device battery in one or more of: battery type; maximum voltage; and capacity.

The first device PCBA can differ from the second device PCBA in one or more of: memory; user programmability; heater control; and feedback functionality.

The control device can include a device window present in the device outer housing, said window being positioned to provide visual access into the device chamber.

The control device can include a device light source and at least one opening through the device outer housing through which light from the device light source is visible.

The outer wall of the tank of the cartridge can be transparent or translucent.

The distal end of the mouthpiece of the cartridge can include a rim wall that is inset from the mouthpiece wall and that engages an interior of the proximal end of the tank.

The mouthpiece can include an interior upper wall between the proximal end and the distal end and also includes an interior lower wall between the upper wall and the distal end of the mouthpiece.

The mouthpiece wall, the interior upper wall, and the interior lower wall can define a vaporization chamber wherein the heater is positioned.

The upper wall can include an opening through which vapor from the vaporization chamber passes toward the exit portal.

The lower wall can include an aperture through which the liquid transport element extends between the heater and the tank.

Electrical contacts can be positioned in the mouthpiece wall.

The mouthpiece wall can include a flange positioned between the proximal end and the distal end thereof.

The electrical contacts can be positioned in the mouthpiece wall between the flange and the distal end of the mouthpiece.

The opening at the device proximal end can include a recess with an inwardly projecting lip.

The flange of the mouthpiece can be configured to be at least partially received within the recess so as to contact the inwardly projecting lip.

One or more of the following conditions can be met: the flange comprises a magnetic component and the inwardly projecting lip comprises a metal component configured for magnetic attraction; the inwardly projecting lip comprises a magnetic component and the flange comprises a metal component configured for magnetic attraction; the flange comprises a magnetic component and the inwardly projecting lip comprises a magnetic component.

The cartridge can comprise an air entry positioned in the outer mouthpiece wall.

The control device can comprise a pressure drop aperture positioned in the device inner frame.

The system can comprise a first cartridge and a second cartridge that is different from the first cartridge.

The first cartridge can include a first heater, and the second cartridge includes a second heater that is different from the first heater.

The first cartridge can include a first tank having a first volume, and the second cartridge includes a second tank having a second volume that is different from the first volume of the first tank.

The first cartridge can include a first liquid transport element, and the second cartridge includes a second liquid transport element that is different from the first liquid transport element.

The vaporization system further can comprise an external connector configured for electrical contact with the control device external connection element.

BRIEF DESCRIPTION OF THE FIGURES

Figure 1:
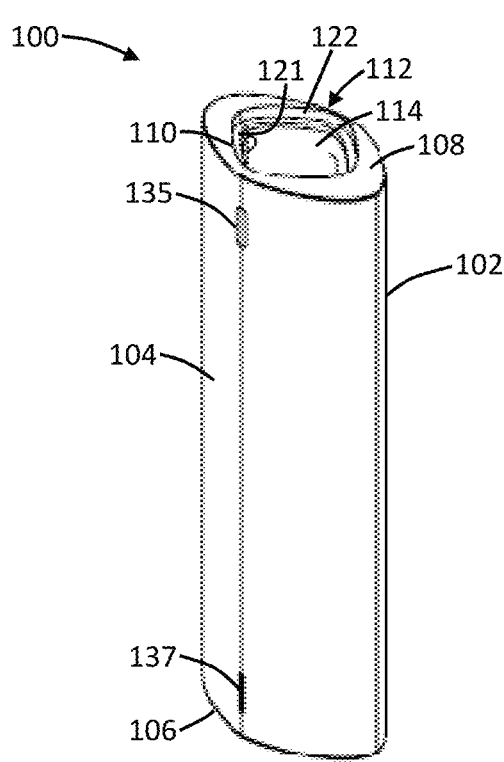
Figure 2:
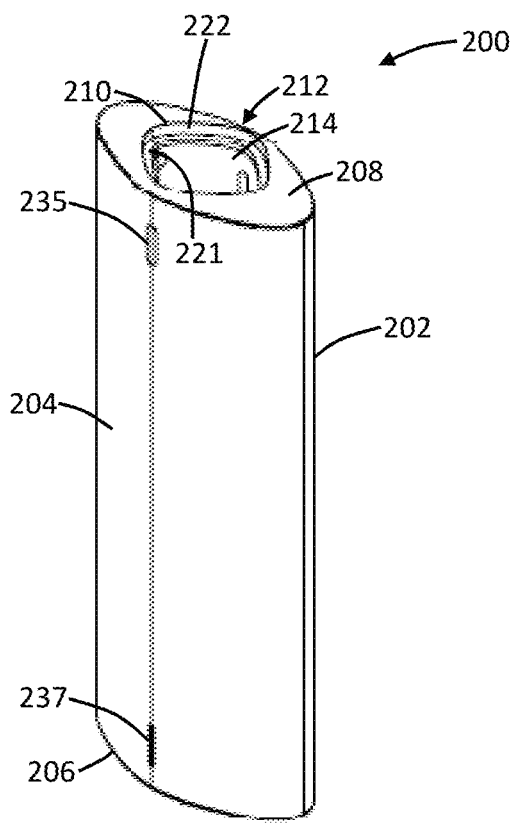
Figure 3:
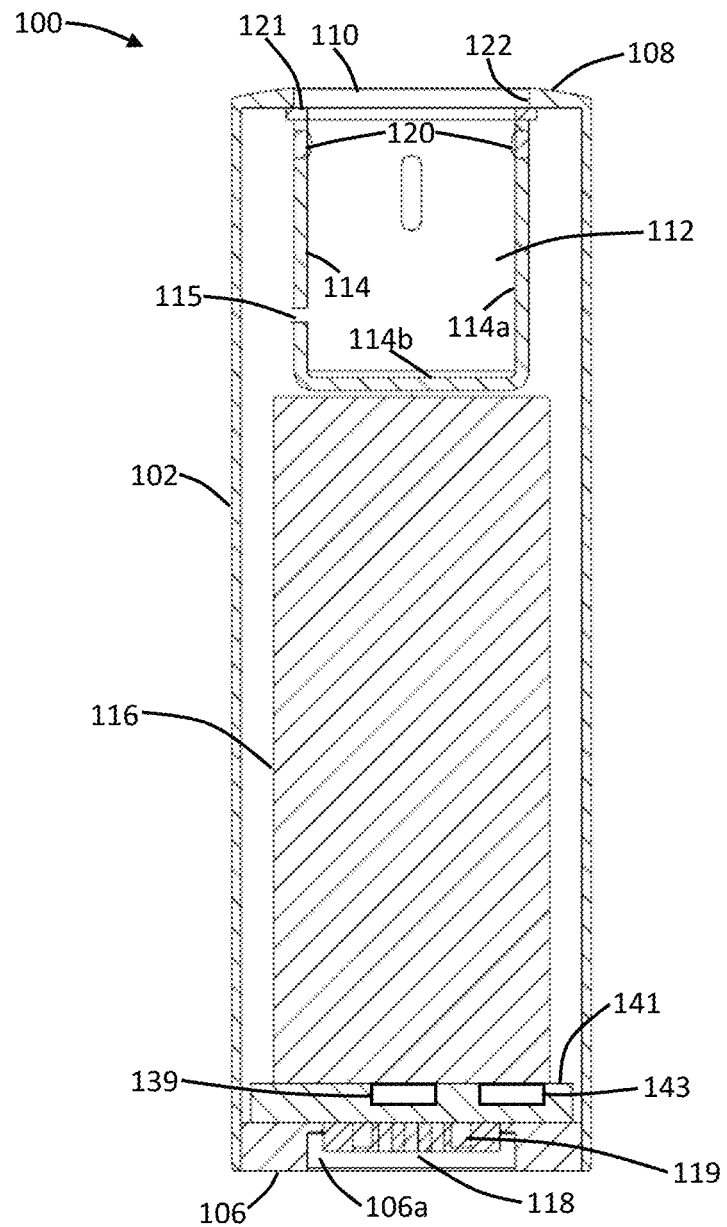
Figure 4:
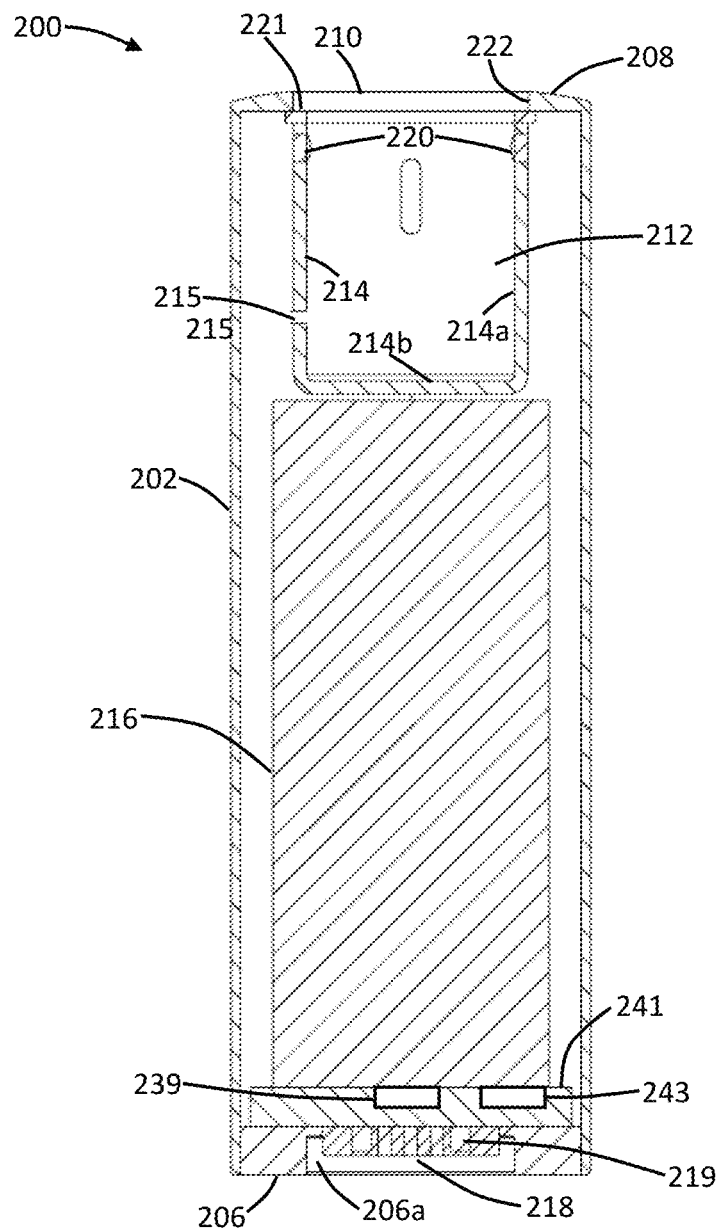

Having thus described the disclosure in the foregoing general terms, reference will now be made to the accompanying drawings, which are not necessarily drawn to scale, and wherein:

FIG. 1 is a perspective view of a device according to example embodiments of the present disclosure;

FIG. 2 is a perspective view of a device according to further example embodiments of the present disclosure;

FIG. 3 is partial cross-section of the device illustrated in FIG. 1;

FIG. 4 is a partial cross-section of the device illustrated in FIG. 2;

FIG. 5 is a perspective view of a cartridge according to example embodiments of the present disclosure;

FIG. 6 is a perspective view of a cartridge according to further example embodiments of the present disclosure;

FIG. 7 is a partial cross-section of the cartridge illustrated in FIG. 5;

FIG. 8 is a partial cross-section of the cartridge illustrated in FIG. 6; and

Figure 9:
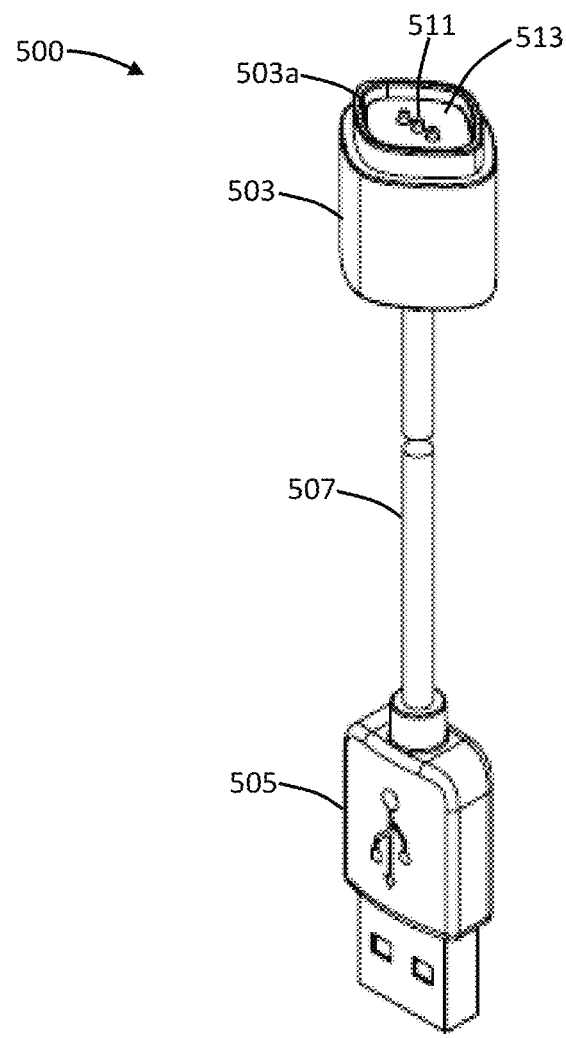

FIG. 9 is perspective view of an external connector according to embodiments of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems or vaporization systems, said terms being used herein interchangeably. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors resulting from volatilization or vaporization of certain components incorporated therein. In various embodiments, components of aerosol delivery systems may be characterized as electronic cigarettes, and those electronic cigarettes may incorporate tobacco and/or components derived from tobacco, and hence deliver tobacco derived components in aerosol form.

Aerosol generating pieces of certain embodiments may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in the background art section of the present disclosure.

In one or more embodiments, the present disclosure relates to a vaporization system that is formed of a plurality of elements that provides for interchangeability of parts to as to provide a consumer-defined combination of parts. For example, the vaporization system can comprise a single control device and at least two different cartridges that can be interchangeably used with at least one control device to provide different vaporization characteristics. As a further example, the vaporization system can comprise at least two different control devices that can be interchangeably used with at least one cartridge to provide different vaporization characteristics. More preferably, as another example, the vaporization system can comprise at least two different control devices that can be interchangeably used with at least two different cartridges to provide different vaporization characteristics. Structural and functional elements making two or more control devices different from one another are evident from the further description of the vaporization system provided herein. Likewise, structural and functional elements making two or more cartridges different from one another are also evident from the further description of the vaporization system provided herein. There is no limit to the number of control devices and cartridges that may be interchangeably utilized in the vaporization system so long as certain standardized elements, as further described herein, are provided. In addition to the control device(s) and the cartridge(s), the vaporization system also includes an external connector that is interchangeably used with one or more control devices. The external connector may be characterized as a charging cord, a communication cord, or the like and is further described herein.

An example embodiment of a first control device 100 for use in a vaporization system of the present disclosure is shown in FIG. 1, and an example embodiment of a second control device 200 for use in a vaporization system of the present disclosure is shown in FIG. 2. Both of a first control device 100 and a second control device 200 are illustrated since the vaporization system can include a plurality of control devices; however, it is understood that, in one or more embodiments, only a single control device may be required for the present vaporization system, such as when a plurality of different cartridges may be included with the vaporization system.

As seen in FIG. 1, the first control device 100 comprises a first device outer housing 102 that defines a first device outer wall 104, a first device distal end 106, and a first device proximal end 108. The first device proximal end 108 includes an opening 110 that provides access to a first device chamber 112 that is defined by a first device inner frame 114. In some embodiments, the first device inner frame 114 may include a pressure drop aperture 115 configured for transferring pressure differentials therethrough to a sensor 143 positioned within the device 100 when air is drawn into the first device chamber 112.

As seen in FIG. 2, the second control device 200 comprises a second device outer housing 202 that defines a second device outer wall 204, a second device distal end 206, and a second device proximal end 208. The second device proximal end 208 includes an opening 210 that provides access to a second device chamber 212 that is defined by a second device inner frame 214. In some embodiments, the second device inner frame 214 may include a pressure drop aperture 215 configured for transferring pressure differentials therethrough to a sensor 243 positioned within the device 200 when air is drawn into the second device chamber 212.

When a vaporization system of the present disclosure comprises two (or more) control devices, it is understood that the control devices will differ from one another in one or more aspects. For example, referring to FIG. 1 and FIG. 2, it is evident that the second device outer housing 202 is larger in dimensions than the first device outer housing 102. Further differences may also exist between respective control devices, as further discussed herein.

The nature of the control devices is further evident in relation to FIG. 3, which shows a partial cross section of the first control device 100. As seen therein, the first control device 100 further includes a first device battery 116 positioned within the first device outer housing 102 and also includes a first device external connection element 118. Preferably, the first device external connection element 118 is positioned at the distal end 106 of the first device outer housing 102. First device electrical connectors 120 are positioned in the first device chamber 112 and, as illustrated, are present in sidewalls 114a of the first device inner frame 114, which frame defines the boundaries of the first device chamber 112. It is understood, though, that the first device electrical connectors 120 may be positioned in the bottom wall 114b of the first device inner frame 114. Moreover, the first device electrical connectors 120 may be present at any position on the sidewalls 114a or the bottom wall 114b of the first device inner frame 114. For example, the first device electrical connectors 120 may be positioned at a point on the sidewalls 114a between the proximal end 108 of the first device outer housing 102 and the bottom wall 114b of the first device inner frame 114. Further, the first device electrical connectors 120 may be positioned between a midpoint of the sidewalls 114a and the proximal end 108 of the first device outer housing 102 (i.e., in an upper half of the sidewalls). Alternatively, the first device electrical connectors 120 may be positioned between a midpoint of the sidewalls 114a and the bottom wall 114b of the first device inner frame 114 (i.e., in a lower half of the sidewalls). In some embodiments, the first device electrical connectors 120 expressly are not present in or on the bottom wall 114b of the first device inner frame 114. In such embodiments, the first device electrical connectors 120 specifically are instead present in or on the sidewalls 114b or are present at the proximal end 108 of the first device outer housing 102.

While FIG. 3 illustrates the first control device 100, it is understood that the elements described in FIG. 3 may also be present in the second control device 200, as shown in FIG. 4. Specifically, the second control device 200 can include a second device battery 216 positioned within the second device outer housing 202 and also include a second device external connection element 218. Preferably, the second device external connection element 218 is positioned at the distal end 206 of the second device outer housing 202. Second device electrical connectors 220 are positioned in the second device chamber 212 and, as illustrated, are present in sidewalls 214a of the second device inner frame 214, which frame defines the boundaries of the second device chamber 212. It is understood, though, that the second device electrical connectors 220 may be positioned in the bottom wall 214b of the second device inner frame 214. Moreover, the second device electrical connectors 220 may be present at any position on the sidewalls 214a or the bottom wall 214b of the second device inner frame 214. For example, the second device electrical connectors 220 may be positioned at a point on the sidewalls 214a between the proximal end 208 of the second device outer housing 202 and the bottom wall 214b of the second device inner frame 214. Further, the second device electrical connectors 220 may be positioned between a midpoint of the sidewalls 214a and the proximal end 208 of the second device outer housing 202 (i.e., in an upper half of the sidewalls). Alternatively, the second device electrical connectors 220 may be positioned between a midpoint of the sidewalls 214a and the bottom wall 214b of the second device inner frame 214 (i.e., in a lower half of the sidewalls). In some embodiments, the second device electrical connectors 220 expressly are not present in or on the bottom wall 214b of the second device inner frame 214. In such embodiments, the second device electrical connectors 220 specifically are instead present in or on the sidewalls 214b or are present at the proximal end 208 of the second device outer housing 202.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference.

As is evident from FIG. 3 and FIG. 4, the first device chamber 112 and the second device chamber 212 are elements separate from the first device outer housing 102 and the second device outer housing 202, respectively. In other words, the chamber is not merely an interior space that is defined by the outer housing. Rather, the inner frame defining the chamber exists independently and separately from the outer housing. The opening of the chamber may coincide with the opening at the proximal end of the outer housing. The inner frame thus may be a completely different element that is attached to the outer housing. Alternatively, the inner frame and the outer housing may be continuously formed. In either case, however, the sidewalls forming the inner frame are present interior to and separated from the outer housing.

The first device outer housing 102 and the second device outer housing 202 may be formed of any suitable material, such as a metal, plastic, ceramic, glass, or the like. Preferably, the first device inner frame 114 and the second device inner frame 214 are formed of the same material as used to form the first device outer housing 102 and the second device outer housing 202; however, different materials may be used. Choice of materials as noted above may also extend to the device outer housing for any further control device(s) that are included in the vaporization system.

The presently disclosed system may comprise a single control device (e.g., the first control device 100 or the second control device 200 or a similar further control device). Such single control device can be interchangeably connectable with a plurality of cartridges to form a plurality of different vaporization systems. For example, the first control device may be interchangeably connectable with a first cartridge to form a first functioning vaporization system having a first set of characteristics, and the first control device may be interchangeably connectable with a second cartridge to form a second functioning vaporization system having a second, different set of characteristics. Such vaporization can comprise two different cartridges, three different cartridges, or an even greater number of different cartridges that are all interchangeable with the first control device.

The presently disclosed system may comprise a plurality of control devices (e.g., the first control device 100 and the second control device 200 and optionally a third control device or an even greater number of control devices). The plurality of control devices can be interchangeably connectable with at least one cartridge to form a plurality of different vaporization systems. For example, the first control device may be interchangeably connectable with a first cartridge to form a first functioning vaporization system having a first set of characteristics, and the second control device may be interchangeably connectable with the first cartridge to form a second functioning vaporization system having a second, different set of characteristics.

There is no limit to the number of control devices and the number of cartridges that may be used to from the vaporization system. A single control device may be separately and interchangeably combined with two, three, four, five, or even more cartridges each having different characteristics to form a functioning vaporization system comprised of a plurality of different systems (e.g., control device one with cartridge one, control device one with cartridge two, etc.). Likewise, a single cartridge may be separately and interchangeably combined with two, three, four, five, or even more control devices each having different characteristics to form a functioning vaporization system comprised of a plurality of different systems (e.g., control device one with cartridge one, control device two with cartridge one, etc.). Further, a plurality of control devices each having different characteristics may be separately and interchangeably combined with a plurality of cartridges each having different characteristics to form a functioning vaporization system comprised of a plurality of different systems (e.g., control device one with cartridge one, control device one with cartridge two, control device two with cartridge one, control device two with cartridge two, etc.). Thus, a vaporization system of the present disclosure can be formed of any number of control devices and any number of cartridges so long as the vaporization system includes at least two different versions of one of the components (i.e., at least two different control devices and/or at least two different cartridges). Factors for determining what causes two control devices to be different and for determining what causes two cartridges to be different are further described herein, and even further differential factors may be realized based upon knowledge of the present disclosure.

An example embodiment of a first cartridge 300 for use in a vaporization system of the present disclosure is shown in FIG. 5, and an example embodiment of a second cartridge 400 for use in a vaporization system of the present disclosure is shown in FIG. 6. Both of a first cartridge 300 and a second cartridge 400 are illustrated since the vaporization system can include a plurality of cartridges; however, it is understood that, in one or more embodiments, only a single cartridge may be required for the present vaporization system, such as when a plurality of different control devices may be included with the vaporization system.

As seen in FIG. 5, the first cartridge 300 comprises a tank 301 that is defined by an outer tank wall 303 that includes a proximal end 305 and a distal end 307 that is closed. As such, the tank 301 may be characterized in that the tank wall 303 is a sidewall that is continuous around the tank, and the distal end 307 defines a bottom wall. The distal end 307 of the tank 301 further can define a bottom end of the cartridge 300. The tank is configured to contain a liquid composition for vaporization—i.e., an e-liquid or aerosol precursor composition, which may be configured as otherwise described herein. The first cartridge 300 further can comprise a mouthpiece 309 that is defined by an outer mouthpiece wall 311 that includes a proximal end 313 with an exit portal 315 and a distal end 317 that is engaging the proximal end 305 of the tank 301. Although the mouthpiece 309 is described as being a separate element from the tank 301, it is understood that the tank wall 303 may extend a greater distance so as to form an integral mouthpiece. As such, the mouthpiece may be attached to the tank, or the mouthpiece may be integrally formed with the tank.

The first cartridge 300 is further illustrated in FIG. 7. As seen therein, the cartridge 300 further includes a heater 319 and a liquid transport element 321 that extends between the heater and a liquid 323 contained within the tank 301. The heater 319 and liquid transport element 321 may be configured as separate elements that are fluidly connected or may be configured as a combined element. Moreover, the heater 319 and the liquid transport element 321 may be formed of any construction as otherwise described herein. The first cartridge 300 also includes one or more electrical contacts 325 that are configured to electrically connect the heater 319 with the battery (116, 216) in one of the control devices (100, 200).

A further cartridge 400 is illustrated in FIG. 6 and FIG. 8 and can be characterized as being a second cartridge 400 in that it differs from the first cartridge 300 in at least one aspect. As such, in relation to FIG. 5 and FIG. 7, the components of the first cartridge 300 may be characterized as being a first tank 301, a first mouthpiece 309, a first heater 319, and so on. In FIG. 6 and FIG. 8, the second cartridge 400 differs from the first cartridge 300 in relation to cartridge size—i.e., the second tank 401 being larger than the first tank 301 in the first cartridge, and the second mouthpiece 409 being larger than the first mouthpiece 309 in the first cartridge. As further described herein, however, two cartridges may differ in a variety of manners.

In FIG. 6 and FIG. 8, the second cartridge 400 comprises a second tank 401 that is defined by an outer tank wall 403 that includes a proximal end 405 and a distal end 407 that is closed. As such, the second tank 401 may be characterized in that the tank wall 403 is a sidewall that is continuous around the tank, and the distal end 407 defines a bottom wall. The distal end 407 of the tank 401 further can define a bottom end of the cartridge 400. The second tank is configured to contain a liquid composition for vaporization—i.e., an e-liquid or aerosol precursor composition, which may be configured as otherwise described herein. The second cartridge 400 further can comprise a second mouthpiece 409 that is defined by an outer mouthpiece wall 411 that includes a proximal end 413 with an exit portal 415 and a distal end 417 that is engaging the proximal end 405 of the second tank 401.

As seen in FIG. 8, the second cartridge 400 further includes a second heater 419 and a second liquid transport element 421 that extends between the second heater and a liquid 423 contained within the tank 401. The second heater 419 and second liquid transport element 421 may be configured as separate elements that are fluidly connected or may be configured as a combined element. Moreover, the second heater 419 and the second liquid transport element 421 may be formed of any construction as otherwise described herein. The second cartridge 400 also includes one or more electrical contacts 425 that are configured to electrically connect the second heater 419 with the battery (116, 216) in one of the control devices (100, 200).

A liquid transport element (321, 421) can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element (321, 421) thus can be any material that contains an open pore network (i.e., a plurality of pores that are interconnected so that fluid may flow from one pore to another in a plurality of direction through the element). As further discussed herein, some embodiments of the present disclosure can particularly relate to the use of non-fibrous transport elements. As such, fibrous transport elements can be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference. In some embodiments, a liquid transport element (321, 421) can be formed partially or completely from a porous monolith, such as a porous ceramic, a porous glass, or the like. Example monolithic materials suitable for use according to embodiments of the present disclosure are described, for example, in U.S. Pat. App. Ser. No. 14/988, 109, filed Jan. 5, 2016, and US Pat. No. 2014/0123989 to LaMothe, the disclosures of which are incorporated herein by reference. The porous monolith can form a substantially solid wick.

Various embodiments of materials configured to produce heat when electrical current is applied therethrough may be employed to form the heater (319, 419). In some embodiments, the heater (319, 419) can be a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further embodiments, the heater (319, 419) can be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater (319, 419) in particular may be configured to be substantially flat. Such heaters are described in U.S. Pat. Pub. No. 2016/0345633 to DePiano et al., which is incorporated herein by reference.

The outer tank wall (303, 403) can be configured to be at least partially transparent or translucent so that the liquid (323, 423) contained therein is visible externally. As such, the entire outer tank wall (303, 403) can be transparent or translucent. Alternatively, only a single side of the outer tank wall (303, 403) can be transparent or translucent while the remaining portions of the outer tank wall can be substantially opaque. In some embodiments, the outer tank wall (303, 403) may be substantially opaque, and a strip (e.g., about 1 mm wide to about 20 mm wide or about 2 mm wide to about 18 mm wide or about 5 mm wide to about 15 mm wide) extending from the proximal end (305, 405) of the tank (301, 401) to the distal end (307, 407) of the tank may be transparent or translucent. In further embodiments, the outer tank wall (303, 403) can be colored. The color can be configured so that the liquid (323, 423) within the tank (301, 401) is still visible, or the color can be configured so that the outer tank wall (303, 403) is substantially opaque.

In one or more embodiments, the mouthpiece (309, 409) of the cartridge (300, 400) can be configured for engagement with the tank (301, 401). For example, as illustrated in FIG. 5 through FIG. 8, the distal end (317, 417) of the mouthpiece (309, 409) can include a rim wall (i.e., a first mouthpiece rim wall 330 and a second mouthpiece rim wall 430) that is at least partially inset from the outer mouthpiece wall (311, 411), and the rim wall can be configured to engage an interior of the proximal end (305, 405) of the outer tank wall (303, 403). The rim wall (311, 411) can have a length of about 1 mm to about 20 mm, about 2 mm to about 18 mm, or about 5 mm to about 15 mm. The rim wall (311, 411) can engage the outer tank wall (303, 403) via a friction fit alone, or the rim wall can be substantially permanently attached to the outer tank wall, such as through welding or gluing.

In some embodiments, the mouthpiece (309, 409) may define substantially only on open interior space through which formed vapor may combine with air to form an aerosol for output through the exit portal (315, 415) of the mouthpiece. In one or more embodiments, the mouthpiece (309, 409) can include one or more further interior walls that can be arranged to define one or more compartments within the mouthpiece. For example, the mouthpiece can include an interior upper wall between the proximal end and the distal end of the mouthpiece and also include an interior lower wall between the interior upper wall and the proximal end of the mouthpiece. More particularly, as seen in FIG. 7, the first mouthpiece 309 can include a first interior upper wall 332 between the first proximal end 313 and the first distal end 317. Likewise, as seen in FIG. 8, the second mouthpiece 409 can include a second interior upper wall 432 between the second proximal end 413 and the second distal end 417. Further, the first mouthpiece 309 can include a first interior lower wall 334 between the first interior upper wall 332 and the first distal end 317 of the mouthpiece. Likewise, the second mouthpiece 409 can include a second interior lower wall 434 between the second interior upper wall 432 and the second distal end 417 of the mouthpiece.

Two or more walls in the mouthpiece can be configured to define a vaporization chamber within which the heater can be positioned. As seen in FIG. 7, the first outer mouthpiece wall 311, the first interior upper wall 332, and the first interior lower wall 334 define a first vaporization chamber 342 wherein the first heater 319 is positioned. Likewise, as seen in FIG. 8, the second outer mouthpiece wall 411, the second interior upper wall 432, and the second interior lower wall 434 define a second vaporization chamber 442 wherein the second heater 419 is positioned. The one or more electrical contacts (325, 425) can be positioned within the portion of the outer mouthpiece wall (311, 411) defining the vaporization chamber (342, 442); however, it is understood that one or more electrical leads may extend from the heater (319, 419) to one or more electrical contacts positioned at a different portion of the outer mouthpiece wall or positioned in the outer tank wall (303, 403). For example, one or more electrical contacts (325, 425) can be positioned along a side of the outer tank wall (303, 403). If desired, electrical contacts (325, 425) may be positioned on or at the distal end (307, 407) of the tank (301, 401). In certain embodiments, the electrical contacts (325, 425) expressly may be excluded from being positioned on or at the distal end (307, 407) of the tank (301, 401), and thus also excluded from being positioned on or at a bottom surface or bottom wall of the cartridge (300, 400). To this end, it is understood that the bottom surface or bottom wall of the cartridge (300, 400) can correspond to the distal end (307, 407) of the tank (301, 401). Excluding the electrical contacts (325, 425) from being positioned at the distal end (307, 407) of the tank (301, 401) can be beneficial to improve the interchangeability of the various devices and cartridges described herein. It is likewise understood that the position of the electrical contacts (325, 425) on the cartridge (300, 400) will substantially correspond to the position of the electrical connectors (120, 220) in the chamber (112, 212) of the device (100, 200). The electrical contacts (325, 425) may be characterized as extending through the outer tank wall (303, 403) or through the outer mouthpiece wall (311, 411). Likewise, the electrical contacts (325, 425) may be characterized as being positioned in the outer tank wall (303, 403) or being positioned in the outer mouthpiece wall (311, 411) so as to be exposed and configured for contact with the electrical connectors (120, 220).

One or more walls of the mouthpiece may also include one or more openings for passage therethrough of one or more further elements of the cartridge (300, 400) or passage of formed vapor/aerosol. For example, the first interior upper wall 332 can include a first vapor opening 333 through which vapor formed in the first vaporization chamber 342 can pass toward the first exit portal 315. Likewise, the second interior upper wall 432 can include a second vapor opening 433 through which vapor formed in the second vaporization chamber 442 can pass toward the second exit portal 415. The vapor opening (333, 433) in the interior upper wall (332, 432) can be substantially centrally located therein and can be substantially aligned with the heater (319, 419) along a longitudinal axis of the cartridge (300, 400). As a further example, the first interior lower wall 334 can include a first wick aperture 335 through which the first liquid transport element 321 (e.g., a wick) can pass between the first heater 319 and the liquid 323 in the first tank 301. Likewise, the second interior lower wall 434 can include a second wick aperture 435 through which the second liquid transport element 421 (e.g., a wick) can pass between the second heater 419 and the liquid 423 in the second tank 401. The wick aperture (335, 435) in the interior lower wall (334, 434) can be substantially centrally located therein and can be substantially aligned with the heater (319, 419) along a longitudinal axis of the cartridge (300, 400).

Two or more walls in the mouthpiece can be configured to define a cooling chamber within which formed aerosol can be allowed to expand and/or cool before passing through the exit portal. As seen in FIG. 7, the first outer mouthpiece wall 311 and the first interior upper wall 332 define a first cooling chamber 344 that receives formed vapor/aerosol from the first heater 319, particularly that receives vapor/aerosol from the first vaporization chamber 342. As such, the formed vapor/aerosol passes from the first vaporization chamber 342 through the first vapor opening 333 into the first cooling chamber 344. Likewise, as seen in FIG. 8, the second outer mouthpiece wall 411 and the second interior upper wall 432 define a second cooling chamber 444 that receives formed vapor/aerosol from the second heater 419, particularly that receives vapor/aerosol from the second vaporization chamber 442. As such, the formed vapor/aerosol passes from the second vaporization chamber 442 through the second vapor opening 433 into the second cooling chamber 444.

The vaporization chamber (342, 442) and the cooling chamber (344, 444) can be configured to have a defined relative volume ratio. In particular, the volume ratio of the vaporization chamber (342, 442) to the cooling chamber (344, 444) can be about 2:1 to about 1:4, about 1:1 to about 1:4, or about 1:1.5 to about 1:3.

If desired, the mouthpiece (309, 409) can include one or more elements configured to reduce or prevent leakage of condensed liquids therefrom. For example, all or a part of the interior of the mouthpiece wall (311, 411) and/or the interior upper wall (332, 432) defining the cooling chamber (344, 444) can be formed from or include an absorptive or adsorptive material configured to hold liquid. Alternatively or additionally, all or a part of the interior of the mouthpiece wall (311, 411) and/or the interior upper wall (332, 432) defining the cooling chamber (344, 444) can be configured to direct liquid back toward the atomization chamber (342, 442), such as through the addition of microchannels or the like.

In one or more embodiments, the cartridge (300, 400) can be configured such that the mouthpiece wall (311, 411) can include a flange positioned between the proximal end (313, 413) and the distal end (317, 417) thereof. For example, referring to FIG. 5 and FIG. 7, a flange 350 can be present and can extend circumferentially from the mouthpiece wall 311 around substantially the entirety of the mouthpiece 309. The distance that the flange 350 extends from the mouthpiece wall 311 can be substantially uniform around the entire circumference of the mouthpiece 309. In some embodiments, the distance that the flange 350 extends from the mouthpiece wall 311 can vary at one or more points around the circumference of the mouthpiece 309. The overall cartridge 300 or the mouthpiece 309 separately can be defined in relation to a longitudinal axis (L), a first transverse axis (T1) that is perpendicular to the longitudinal axis, and a second transverse axis (T2) that is perpendicular to the longitudinal axis and is perpendicular to the first transverse axis. The overall cartridge 300 and/or the mouthpiece 309 thus may be defined in relation to a total length along the longitudinal axis (L), a total width along the first transverse axis (T1), and a total depth along the second longitudinal axis (T2). The length may be greater than the width, which in turn may be greater than the depth. The distance that the flange 350 extends away from the mouthpiece wall 311 may be greater along the second transverse axis (T2) than along the first transverse axis (T1). Thus, in alternative embodiments, the total distance between opposing outer edges of the flange 350 across the mouthpiece 309 along the first transverse axis (T1) may be greater than the total distance between opposing edges of the flange across the mouthpiece along the second transverse axis (T2); the total distance between opposing outer edges of the flange 350 across the mouthpiece 309 along the first transverse axis (T1) may be substantially equal to the total distance between opposing edges of the flange across the mouthpiece along the second transverse axis (T2); or the total distance between opposing outer edges of the flange 350 across the mouthpiece 309 along the first transverse axis (T1) may be less than the total distance between opposing edges of the flange across the mouthpiece along the second transverse axis (T2). In particular embodiments, a distance (d2) between the mouthpiece wall 311 and an outer edge of the flange 350 as measured along the second transverse axis (T2) may be greater than a distance (d1) between the mouthpiece wall and an outer edge of the flange as measured along the first transverse axis (T1). Said distances (d1, d2) particularly may be as measured at about a midpoint of each of the first transverse axis (T1) and the second transverse axis (T2).

Referring to FIG. 6 and FIG. 8, a flange 450 can be present and can extend circumferentially from the mouthpiece wall 411 around substantially the entirety of the mouthpiece 409. The distance that the flange 450 extends from the mouthpiece wall 411 can be substantially uniform around the entire circumference of the mouthpiece 409. In some embodiments, the distance that the flange 450 extends from the mouthpiece wall 411 can vary at one or more points around the circumference of the mouthpiece 409. The overall cartridge 400 or the mouthpiece 409 separately can be defined in relation to a longitudinal axis (L), a first transverse axis (T1) that is perpendicular to the longitudinal axis, and a second transverse axis (T2) that is perpendicular to the longitudinal axis and is perpendicular to the first transverse axis. Moreover, the measurements described above in relation to the cartridge 300 in FIG. 5 and FIG. 6 can apply equally to the cartridge 400.

The electrical contacts (325, 425), when present in the mouthpiece wall (311, 411) preferably can be positioned longitudinally between the flange (350, 450) and the distal end (317, 417) of the mouthpiece (309, 409). Further, in some embodiments, the flange (350, 450) can be substantially in line with the interior upper wall (332, 432). As such, the flange (35, 450) can be substantially parallel with and/or may be substantially in the same horizontal plane with the interior upper wall (332, 432). Preferably, the flange (350, 450) is positioned above the vaporization chamber (342, 442) and above the heater (319, 419) along the longitudinal axis (L) of the mouthpiece (309, 409).

The flange (350, 450) can interact with a corresponding lip on the control device (100, 200) to ensure proper connection of the cartridge (300, 400) with the control device. For example, referring to FIG. 1, the first device 100 can be configured so that the opening 110 at the first device proximal end 108 includes a recess with a first inwardly projecting lip 121. The recess thus may comprise a first rim wall 122 that is substantially parallel with the longitudinal axis of the device 100. The first rim wall 122 extends downwardly from the proximal end 108 a short distance, which distance can substantially correspond to a thickness of the flange (350, 450) of the cartridge (300, 400) and/or the thickness of a further element that may be present adjacent the flange. For example, the first rim wall 122 forming the downwardly extending recess may have a height (i.e., as measured from a top surface of the inwardly projecting lip 121 to the first device proximal end 108) of about 1 mm to about 8 mm, about 1 mm to about 6 mm, or about 1 mm to about 5 mm. The first inwardly projecting lip 121 may have a width (i.e., the distance the lip extends inward from the rim wall 122 to a terminal end) of about 1 mm to about 8 mm, about 1 mm to about 6 mm, or about 1 mm to about 5 mm. The first inwardly projecting lip 121 may have a substantially constant width around the entire circumference of the opening 110. In some embodiments, the first inwardly extending lip 121 may be discontinuous and thus may be formed of one or a plurality of inwardly extending lips spaced around the opening 110.

Referring to FIG. 2, the second device 200 likewise can be configured so that the opening 210 at the second device proximal end 208 includes a recess with a second inwardly projecting lip 221. The recess thus may comprise a second rim wall 222 that is substantially parallel with the longitudinal axis of the second device 200. The second rim wall 222 extends downwardly from the second proximal end 208 a short distance, which distance can substantially correspond to a thickness of the flange (350, 450) of the cartridge (300, 400) and/or the thickness of a further element that may be present adjacent the flange. For example, the second rim wall 222 forming the downwardly extending recess may have a height (i.e., as measured from a top surface of the inwardly projecting lip 121 to the first device proximal end 108) of about 1 mm to about 8 mm, about 1 mm to about 6 mm, or about 1 mm to about 5 mm. The second inwardly projecting lip 121 may have a width (i.e., the distance the lip extends inward from the rim wall 122 to a terminal end) of about 1 mm to about 8 mm, about 1 mm to about 6 mm, or about 1 mm to about 5 mm. The second inwardly projecting lip 121 may have a substantially constant width around the entire circumference of the opening 110. In some embodiments, the second inwardly extending lip 121 may be discontinuous and thus may be formed of one or a plurality of inwardly extending lips spaced around the opening 110.

In one or more embodiments, the flange (350, 450) of the mouthpiece (309, 409) is configured to be at least partially received within the recess formed by the rim wall (122, 222) so as to contact the inwardly projecting lip (121, 221). As such, a bottom surface of the flange (350, 450) may be substantially in contact with the inwardly projecting lip (121, 221), and an outer edge of the flange may be substantially adjacent the rim wall (122, 222).

The flange (350, 450) and/or the inwardly projecting lip (121, 221) may be configured to bias the cartridge (300, 400) into connection with the device (100, 200). For example, a magnetic connection may be utilized. As illustrated in FIG. 7 and FIG. 8, the first cartridge 300 may include a first magnet 352 positioned adjacent a bottom surface of the first flange 350, and the second cartridge 400 may include a second magnet 452 positioned adjacent a bottom surface of the second flange 450. The magnet (352, 452) may extend substantially completely around the circumference of the mouthpiece (309, 409) or may be discontinuous so as be configured as one or a plurality of discrete magnets. The magnet (352, 452) may be adhered to the mouthpiece wall (311, 411), may be adhered to the flange (350, 450), or may be adhered to both the mouthpiece wall and the flange. The inwardly projecting lip (121, 221) may be formed of a metal or other material to which the magnet (352, 452) will be attracted by magnetic force. In further embodiments, the magnet (352, 452) may be positioned on the first device 100 or second device 200. Specifically, the magnet (352, 452) may be adhered to the inwardly extending lip (121, 221). In such embodiments, the flange (350, 450) may be formed of a metal or other material to which the magnet (352, 452) will be attracted by magnetic force. In further embodiments, the magnet (352, 452) may be present on the cartridge (300, 400) as well as the device (100, 200). As such, a magnet present adjacent the lower surface of the flange (350, 450) on the cartridge (300, 400) may be attracted by magnetic force to a magnet present adjacent the upper surface of the inwardly projecting lip (121, 221) on the device (100, 200). When a magnet (352, 452) is present on the mouthpiece (309, 409), it is preferable that the combined thickness of the magnet and the flange (350, 450) is substantially identical to the height of the rim wall (122, 222) on the device (100, 200) so that an upper surface of flange is substantially flush with the proximal end (108, 208) of the device when the cartridge and the device are engaged.

As described above, one or both of the first device 100 and the second device 200 (or even further devices) can be configured to be interchangeably connectable with one or both of the first cartridge 300 and the second cartridge 400 (or even further cartridges) such that at least a portion of the tank (301, 401) is separately receivable within the chamber (112, 212) of the device (100, 200) to form the vaporization system in a functioning combination. The vaporization system can be configured so that different combinations of a device (100, 200) and a cartridge (300, 400) result in a system with one or more different functionalities. As such, two or more cartridges combinable with a single device may exhibit one or more different structures and/or functions. Likewise, two or more devices combinable with a single cartridge may exhibit one or more different structures and/or functions.

In some embodiments, a vaporization system comprising at least two devices and at least one cartridge can be configured so that the at least two devices differ from one another in one or more aspects. For example, a first control device can differ from a second control device in that the first device outer housing and the second device outer housing are each formed of a different material. As a further example, an outer wall of a first device and an outer wall of a second device can each have a different surface finish. In still another example, a battery in a first device can be different from a battery in a second device (e.g., differing in one or more of battery type, maximum voltage, and capacity). In yet a further example, a PCBA in a first device can be different from a PCBA in a second device (e.g., the PCBA's may differ in one or more of memory, user programmability, heater control capability, and feedback functionality). In still a further example, an external connection element of a first device can be different from an external connection element on a second device.

In further embodiments, a vaporization system comprising at least two cartridges and at least one device can be configured so that the at least two cartridges differ from one another in one or more aspects. For example, a first cartridge can include a first heater, and a second cartridge can include a second heater that is different from the first heater. As another example, a first cartridge can include a first tank having a first volume, and a second cartridge can include a second tank having a second volume that is different from the first volume of the first tank. In yet another example, a first cartridge can include a first liquid transport element, and a second cartridge can include a second liquid transport element that is different from the first liquid transport element.

The device (100, 200) can be configured in some embodiments so that at least a portion of the tank (301, 401) is visible when the cartridge (300, 400) is engaged with the device. As noted above, at least a portion of the outer tank wall (303, 403) can be configured to be at least partially transparent or translucent so that the liquid (323, 423) contained therein is visible externally. As such, the outer wall (104, 204) of the device (100, 200) can be configured to include a window through which the outer tank wall (303, 403) and optionally any liquid (323, 423) present in the tank (301, 401) can be visible when the cartridge (300, 400) is engaged with the device (100, 200). As seen in FIG. 1, a first window 135 is configured as a cut-out in the outer wall 104 of the device 100 that is positioned near the proximal end 108 of the device. The window preferably is positioned to provide visual access into the first device chamber 112. As illustrated, the cut-out is substantially oval-shaped; however, it is understood that any shape is encompassed herein. In some embodiments, the window 135 may be configured as a notch extending from the proximal end 108 of the outer wall 104 of the device 100 a distance toward the distal end 106 of the device. In other embodiments, the window 135 may be configured to not have any open borders and thus may expressly exclude a notch configuration as noted above. In certain embodiments, a window 135 may be expressly excluded from the device 100. Moreover, the window 135 may be completely open or the window may have a transparent member (e.g., glass or plastic) positioned in the opening defined by the window or covering the window on one or both of the inner surface and outer surface of the outer wall 104 of the device 100.

As seen in FIG. 2, a second window 235 is configured as a cut-out in the outer wall 204 of the device 200 that is positioned near the proximal end 208 of the device. The window preferably is positioned to provide visual access into the second device chamber 212. As illustrated, the cut-out is substantially oval-shaped; however, it is understood that any shape is encompassed herein. In some embodiments, the window 235 may be configured as a notch extending from the proximal end 208 of the outer wall 204 of the device 200 a distance toward the distal end 206 of the device. In other embodiments, the window 235 may be configured to not have any open borders and thus may expressly exclude a notch configuration as noted above. In certain embodiments, a window 235 may be expressly excluded from the device 200. Moreover, the window 235 may be completely open or the window may have a transparent member (e.g., glass or plastic) positioned in the opening defined by the window or covering the window on one or both of the inner surface and outer surface of the outer wall 204 of the device 200.

In one or more embodiments, the first device 100 may include a first light source 139 and at least one opening 137 through the outer wall 104 of the first device through which light from the first light source is visible. The first light source 139 may comprise, for example, one or more light emitting diodes (LED) capable of providing one or more colors of lighting. As illustrated in FIG. 3, the first light source 139 can be positioned directly on the printed circuit board (PCB) 141 on which further control components (e.g., a microcontroller and/or memory components) may be included. The opening 137 may be provided in any desired shape and may particularly be positioned near the distal end 106 of the first device 100. The opening 137 may be completely open or may be filled, such as with a light guide material, or may be covered with a transparent or translucent member (e.g., glass or plastic) on one or both of the inner surface and the outer surface of the outer wall 104 of the device 100. Likewise, the second device 200 may include a second light source 239 and at least one opening 237 through the outer wall 204 of the second device through which light from the second light source is visible. The second light source 239 may comprise, for example, one or more light emitting diodes (LED) capable of providing one or more colors of lighting. As illustrated in FIG. 4, the second light source 239 can be positioned directly on the printed circuit board (PCB) 241 on which further control components (e.g., a microcontroller and/or memory components) may be included. The opening 237 may be provided in any desired shape and may particularly be positioned near the distal end 206 of the second device 200. The opening 237 may be completely open or may be filled, such as with a light guide material, or may be covered with a transparent or translucent member (e.g., glass or plastic) on one or both of the inner surface and the outer surface of the outer wall 204 of the device 200. The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

An airflow sensor, pressure sensor, or the like may be included in the device. For example, as shown in FIG. 3, the first device 100 can include a sensor 143 on the PCB 141. Configurations of a printed circuit board and a pressure sensor, for example, are described in U.S. Pat. Pub. No. 2015/0245658 to Worm et al., the disclosure of which is incorporated herein by reference. The sensor 143 can be positioned anywhere within the first device 100 so as to subject to airflow and/or a pressure change that can signal a draw on the device and thus cause the battery 116 to delivery power to the heater (319, 419) in the cartridge (300, 400). For example, the sensor 143 may be positioned in the area of the proximal end 108 of the device 100, such as at or near the sidewalls 114a or the bottom wall 114b of the first device chamber 112. Likewise, as shown in FIG. 4, the second device 200 can include a sensor 243 on the PCB 241; however, the sensor can be positioned anywhere within the second device 200, such as described immediately above. Alternatively, in the absence of an airflow sensor, the heater (319, 419) may be activated manually, such as by a push button. Additional representative types of sensing or detection mechanisms, structure and configuration thereof, components thereof, and general methods of operation thereof, are described in U.S. Pat. No. 5,261,424 to Sprinkel, Jr.; 5,372,148 to McCafferty et al.; and PCT WO 2010/003480 to Flick; which are incorporated herein by reference.

In use, when a cartridge (300, 400) is inserted into the device chamber (112, 212), the fit may be such that air is capable of passing between the outer surface of the tank wall (303, 403) and the inner surface of the device inner frame (112, 212). Thus, when a user puffs on the mouthpiece (309, 409), air may pass between the outer surface of the tank wall (303, 403) and the inner surface of the device inner frame (112, 212), pass through an air entry (320, 420) in the cartridge (300, 400), pass through the vaporization chamber (342, 442) to mingle with formed vapor, pass through the cooling chamber (344, 444), and ultimately pass through the exit portal (315, 415). The air entry (320, 420) may be specifically positioned in the mouthpiece wall (311, 411). Alternatively, the air entry (320, 420) may be positioned in the tank wall (303, 403). The passage of air as defined above may be effective to cause pressure drop in the device (100, 200) that can be sensed by the sensor (143, 243) through the pressure drop aperture (115, 215).

An input element may be included with the aerosol delivery device (and may replace or supplement an airflow or pressure sensor). The input may be included to allow a user to control functions of the device and/or for output of information to a user. Any component or combination of components may be utilized as an input for controlling the function of the device (100, 200). For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included, choosing the total particulate matter (TPM) provided per puff, choosing a specific heating profile to be implemented, choosing a modifiable resistance to drawn, and the like.

Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and 8,539,959 to Scatterday; U.S. Pat. Pub. No. 2015/0020825 to Galloway et al.; and U.S. Pat. Pub. No. 2015/0216233 to Sears et al.; which are incorporated herein by reference. It is understood that not all of the illustrated elements are required. For example, an LED may be absent or may be replaced with a different indicator, such as a vibrating indicator. Likewise, a flow sensor may be replaced with a manual actuator, such as a push button.

In one or more embodiments, the vaporization system formed by any combination of one or device(s) and one or more cartridge(s) can further include an external connector 500 configured for electrical contact with each of the device external connection element (e.g., first device external connection element 118 and the second device external connection element 218). The external connector 500 can include a first connector end 503 and a second connector end 505 interconnected by a union 507, which may be, for example, a cord of variable length. The first connector end 503 can be configured for electrical and, optionally, mechanical connection with the device (100, 200). In particular, the first connector end 503 can include an inset wall 503a that can be received within a well (e.g., first well 106a at the distal end 106 of the first device 100 or the second well 206b at the distal end 206 of the second device 200) present at the distal end (106, 206) of the device (100, 200). The external connector 500 can include a plurality of electrical pins 511 interior to the inset wall 503a configured for making a charging and/or information transferring connection with the device external connection element (118, 218). In some embodiments, the device (100, 200) can include a mechanical connector (e.g., first mechanical connector 119 and second mechanical connector 219) adjacent the device external connection element (118, 218). The mechanical connector (119, 219) can be a magnet or a metal (or like element) that is adapted for magnetic attraction to a magnet. The first connector end 503 then can likewise include a mechanical connection element 513 that is positioned between the inset wall 503a and the electrical pins 511. The mechanical connection element 513 can be a magnet or a metal (or like element) that is adapted for magnetic attraction to a magnet. The second connector end 505 can be configured for connection to a computer or similar electronic device or for connection to a power source. As illustrated, the second connector end 505 has a Universal Serial Bus (USB) connection; however, a different connection may also be provided and/or an adapter may likewise be included (e.g., a USB/AC adapter). For example, an adaptor including a USB connector at one end and a power unit connector at an opposing end is disclosed in U.S. Pat. Pub. No. 2014/0261495 to Novak et al., which is incorporated herein by reference.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine). In some embodiments, an aerosol precursor composition may comprise nicotine in a free-base form and/or a protonated form. Protonation may be achieved through inclusion of one or more acids in the aerosol precursor composition. For example, organic acids, such as levulinic acid, succinic acid, lactic acid, and pyruvic acid, may be included in the aerosol precursor with nicotine in amounts up to being equimolar (based on total organic acid content) with the nicotine. Any combination of organic acids can be used. For example, the aerosol precursor can include about 0.1 to about 0.5 moles of any one or more of the above-noted organic acids per one mole of nicotine, up to a concentration wherein the total amount of organic acid present is equimolar to the total amount of nicotine present in the aerosol precursor composition.

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 1 ml or more, about 2 ml or more, about 5 ml or more, or about 10 ml or more of the aerosol precursor composition may be included.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:
1. A vaporization system comprising:
   a control device having:
      a device outer housing defining a device outer wall, a device distal end, and a device proximal end that includes an opening formed therein;
      a device chamber defined by a device inner frame having at least a chamber sidewall and a chamber bottom wall, the opening in the device proximal end providing access into the device chamber;
      a device battery positioned within the device outer housing;
      a device printed circuit board assembly (PCBA) positioned within the device outer housing;
      device electrical connectors positioned in the device chamber; and
      a device external connection element;
   a cartridge comprising:
      a tank defined by an outer tank wall that includes a closed end and an opposing end comprising a wall having an aperture defined therein, the tank being configured to contain a liquid composition;
      a mouthpiece defined by an outer mouthpiece wall that includes a proximal end with an exit portal and a distal end that is engaging the tank;
      a heater;
      a liquid transport element at least partially inserted into the aperture defined in the wall of the opposing end of the tank, the liquid transport element being effective to deliver the liquid composition from the tank to the heater; and electrical contacts;

wherein the aperture defined in the wall of the opposing end of the tank, the liquid transport element, and the heater are centrally located and aligned along a longitudinal axis of the cartridge; and wherein the cartridge is configured to engage the control device such that at least a portion of the tank of the cartridge is received within the device chamber to form the vaporization system in a functioning combination with the electrical contacts of the cartridge electrically engaging the device electrical connectors.

2. The vaporization system of claim 1, the vaporization system comprising a first control device and a second control device, wherein the first control device and the second control device are interchangeably connectable with the cartridge such that at least a portion of the tank of the cartridge is separately receivable within each of a first control device chamber present in the first control device and a second control device chamber present in the second control device to form the vaporization system in a functioning combination, and wherein the first control device differs from the second control device.

3. The vaporization system of claim 2, wherein the first control device differs from the second control device in one or more of the following aspects:

the first control device comprises a first control device outer housing, and the second control device comprises a second control device outer housing, and the first control device outer housing and the second control device outer housing are each formed of a different material;

the first control device comprises a first control device battery, and the second control device comprises a second control device battery, and the first control device battery is different from the second control device battery;

the first control device comprises a first control device PCBA, and the second control device comprises a second control device PCBA, and the first control device PCBA is different from the second control device PCBA; and the first control device comprises a first control device external connection element, and the second control device comprises a second control device external connection element, and the first control device external connection element is different from the second control device external connection element.

4. The vaporization system of claim 3, wherein the first control device battery differs from the second control device battery in one or more of: battery type; maximum voltage; and capacity.

5. The vaporization system of claim 3, wherein the first control device PCBA differs from the second control device PCBA in one or more of: memory; user programmability; heater control; and feedback functionality.

6. The vaporization system of claim 1, wherein the control device includes a device window present in the device outer housing, said window being positioned to provide visual access into the device chamber.

7. The vaporization system of claim 1, wherein the control device includes a device light source and at least one opening through the device outer housing through which light from the device light source is visible.

8. The vaporization system of claim 1, wherein the outer wall of the tank of the cartridge is transparent or translucent.

9. The vaporization system of claim 1, wherein the distal end of the mouthpiece of the cartridge includes a rim wall that is inset from the outer mouthpiece wall and that engages an interior of the proximal end of the tank.

10. The vaporization system of claim 1, wherein the heater is positioned within a vaporization chamber.

11. The vaporization system of claim 1, wherein electrical contacts are positioned in the mouthpiece wall.

12. The vaporization system of claim 1, wherein the mouthpiece wall includes a flange positioned between the proximal end and the distal end thereof.

13. The vaporization system of claim 12, wherein the electrical contacts are positioned in the mouthpiece wall between the flange and the distal end of the mouthpiece.

14. The vaporization system of claim 12, wherein the opening at the device proximal end includes a recess with an inwardly projecting lip.

15. The vaporization system of claim 14, wherein the flange of the mouthpiece is configured to be at least partially received within the recess so as to contact the inwardly projecting lip.

16. The vaporization system of claim 15, wherein one or more of the following conditions is met:

the flange comprises a magnetic component and the inwardly projecting lip comprises a metal component configured for magnetic attraction;

the inwardly projecting lip comprises a magnetic component and the flange comprises a metal component configured for magnetic attraction;

the flange comprises a magnetic component and the inwardly projecting lip comprises a magnetic component.

17. The vaporization system of claim 1, wherein the cartridge comprises an air entry positioned in a wall thereof.

18. The vaporization system of claim 1, wherein the control device comprises a pressure drop aperture positioned in the device inner frame.

19. The vaporization system of claim 1, wherein the system comprises a first cartridge and a second cartridge that is different from the first cartridge.

20. The vaporization system of claim 19, wherein the first cartridge includes a first heater, and the second cartridge includes a second heater that is different from the first heater.

21. The vaporization system of claim 19, wherein the first cartridge includes a first tank having a first volume, and the second cartridge includes a second tank having a second volume that is different from the first volume of the first tank.

22. The vaporization system of claim 19, wherein the first cartridge includes a first liquid transport element, and the second cartridge includes a second liquid transport element that is different from the first liquid transport element.

23. The vaporization system of claim 1, further comprising an external connector configured for electrical contact with the control device external connection element.

* * * * *